US008864716B2

United States Patent
Scholly et al.

(10) Patent No.: US 8,864,716 B2
(45) Date of Patent: Oct. 21, 2014

(54) DEVICE FOR MONITORING AND/OR MANIPULATING OBJECTS ARRANGED IN A CAVITY THAT CAN BE ACCESSED THROUGH A NARROW OPENING

(75) Inventors: Werner Scholly, Denzlingen (DE); Axel Hofer, Endingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 38 days.

(21) Appl. No.: 13/579,963

(22) PCT Filed: Dec. 16, 2010

(86) PCT No.: PCT/EP2010/007710
§ 371 (c)(1),
(2), (4) Date: Aug. 20, 2012

(87) PCT Pub. No.: WO2011/103903
PCT Pub. Date: Sep. 1, 2011

(65) Prior Publication Data
US 2012/0316494 A1    Dec. 13, 2012

(30) Foreign Application Priority Data

Feb. 23, 2010  (DE) .................. 10 2010 008 922

(51) Int. Cl.
| | | |
|---|---|---|
| A61M 5/178 | (2006.01) | |
| A61M 25/01 | (2006.01) | |
| G02B 23/24 | (2006.01) | |
| A61B 1/008 | (2006.01) | |
| A61B 1/005 | (2006.01) | |

(52) U.S. Cl.
CPC ........ *A61M 25/0136* (2013.01); *G02B 23/2476* (2013.01); *A61B 1/008* (2013.01); *A61B 1/0055* (2013.01); *A61B 1/0052* (2013.01); *A61B 1/0057* (2013.01); *A61M 25/0133* (2013.01)
USPC ..................................... 604/170.03

(58) Field of Classification Search
CPC ................... A61B 2017/003; A61M 25/0105; A61M 25/0133; A61M 25/0147
USPC ..................................... 604/523, 528, 170.03
See application file for complete search history.

(56) References Cited

U.S. PATENT DOCUMENTS

| | | | |
|---|---|---|---|
| 5,395,342 A * | 3/1995 | Yoon | 604/167.03 |
| 5,478,318 A * | 12/1995 | Yoon | 604/167.05 |
| 6,569,105 B1 | 5/2003 | Kortenbach et al. | |
| 7,874,308 B2 * | 1/2011 | Kessell et al. | 137/68.3 |
| 8,118,783 B2 * | 2/2012 | Smith | 604/164.04 |
| 2006/0217666 A1 * | 9/2006 | Wenchell | 604/167.03 |
| 2007/0282371 A1 | 12/2007 | Lee et al. | |
| 2012/0316494 A1 * | 12/2012 | Scholly et al. | 604/95.04 |

FOREIGN PATENT DOCUMENTS

| | | |
|---|---|---|
| EP | 1915950 | 4/2008 |
| EP | 2005896 | 12/2008 |
| WO | 2008101228 | 8/2008 |

* cited by examiner

*Primary Examiner* — Aarti B Berdichevsky
(74) *Attorney, Agent, or Firm* — Volpe and Koenig, P.C.

(57) ABSTRACT

In a device (1) for monitoring and/or manipulating objects that are arranged in a cavity that can be accessed through a narrow opening, a tubular or hose-shaped insertion part (2) is provided, on which a flexible section (4) is formed, which can be controlled by a Bowden cable (5), the Bowden cable (5) acting on an actuating element (10) which is rotatably supported in a joint (11) which includes a joint socket (13) and a corresponding joint ball (12) that engages with the joint socket (13).

10 Claims, 4 Drawing Sheets

DEVICE FOR MONITORING AND/OR MANIPULATING OBJECTS ARRANGED IN A CAVITY THAT CAN BE ACCESSED THROUGH A NARROW OPENING

BACKGROUND

The invention relates to a device for monitoring and/or manipulating objects that are arranged in a cavity that can be accessed through a narrow opening, in particular for use in minimally invasive medicine, with a tubular or hose-shaped insertion part, wherein a flexible section is formed on the insertion part, and at least one Bowden cable for controlling the flexible section is arranged in the insertion part, wherein the insertion part contains a guide channel, which is designed to receive optical, mechanical and/or electrical connectors for the monitoring and/or manipulation, and wherein an adjusting element is provided, which is connected to the Bowden cable in order to control the flexible section. Here, the distal end is the end which, in the position of use, is arranged away from a user, while the proximal end is the end which, in the position of use, is arranged near the user.

Devices of this kind are known and have become established.

SUMMARY

The object of the invention is to make available a device of the abovementioned kind that has the smallest possible structural dimensions at the proximal end of the insertion part.

To achieve the object in a device of the abovementioned kind, provision is made, according to the invention, that the adjusting element is arranged on a proximal end of the insertion part, that a joint with a joint socket and with a corresponding joint ball is formed on the proximal end of the insertion part, that the adjusting element is mounted in the joint, and that the adjusting element has a passage, which passage is designed to receive the optical, mechanical and/or electrical connectors, and which passage opens into the proximal end of the guide channel when the adjusting element is in the position of use. The insertion part can be inserted through the opening of the cavity, and monitoring and/or maneuvering mechanisms, which are connected to the connectors, can be provided on the distal end of the insertion part. The invention makes use of the surprising finding that, by designing a joint with joint socket and joint ball instead of the known pivot joints, the interior of the adjusting element can be used for the passage of the connecting lines. Thus, the connecting line does not have to be guided around the adjusting element, which saves space. A further advantage is that the passage, for example if it runs through a rotation point of the joint, changes its orientation and position only slightly during an actuation movement or displacement. This has the additional effect that the connectors arranged in the passage and in the guide channel, i.e. mechanical, optical and/or electrical connecting lines, are affected to the least possible extent by the displacements of the adjusting element. The connecting lines are therefore unstressed.

The passage can be designed as a hole, bore or channel, or in some other way.

Preferably, the passage has a mouth at both of its ends and thus extends the guide channel. Here, provision can be made that the mouth directed away from the guide channel opens into a secondary guide channel in the position of use.

In a solution of independent importance for a device of the type mentioned at the outset, provision can be made that a handle for the insertion part is arranged on a proximal end of the insertion part, that an actuating mechanism for manual actuation of the adjusting element is provided, and that the actuating mechanism is connected to the handle via a flexible control line. Here, provision can additionally be made that a joint with a joint socket and with a corresponding joint ball is formed on the proximal end of the insertion part, that the adjusting element is mounted in the joint, and that the adjusting element has a passage, which passage is designed to receive the optical, mechanical and/or electrical connectors, and which passage opens into a proximal end of the guide channel when the adjusting element is in the position of use. It is advantageous that, by means of the flexible control line, the actuating mechanism can be arranged away from the proximal end of the insertion part. Thus, the required structural dimensions are reduced directly at the proximal end of the insertion part. In addition, the insertion part is relieved upon actuation of the flexible section on the actuating part, because the flexible control line provides a mechanical decoupling between actuating mechanism and insertion part against unwanted reaction movements during the actuation.

To form the joint, provision can be made that the joint socket is formed on the adjusting element, and the joint ball is formed on the proximal end of the insertion part. Conversely, provision can alternatively be made that the joint socket is formed on the proximal end of the insertion part, and the joint ball is formed on the adjusting element.

Here, the joint socket and/or the joint ball can have a contact surface, which describes a portion of a cylindrical surface. Thus, the adjusting element can be designed for two-way control. Provision can also be made that the contact surface describes a spherical or ellipsoid surface. In this way, four-way control of the adjusting element is permitted.

An actuating mechanism can be provided for manual actuation of the adjusting element.

In order to relieve the insertion part during manual actuation of the adjusting element, provision can be made that the actuating mechanism is connected to the adjusting element via a flexible control line. The connection can be produced directly or indirectly via a coupling. It is thus possible to avoid a situation where opposing forces, which are generated during the manual actuation of the actuating mechanism, are transferred to the insertion part inserted into the narrow opening during use.

Provision can be made that a coupling point for form-fit and preferably releasable connection to a mating coupling piece is formed on the adjusting element. Thus, the insertion part can be easily connected for use to the rest of the device and, after use, can even be removed from the latter, which is particularly useful if a sterile or sterilized insertion part is required during use.

In a device that takes up very little space in the area of the opening during use, provision can be made that the adjusting element is arranged in a handle formed on the proximal end of the insertion part.

Advantageous application properties are achieved if the at least one Bowden cable and the adjusting element and/or the actuating mechanism are designed for two-way or four-way control of the flexible section. For this purpose, two or four Bowden cables are arranged in a manner known per se in the insertion part, and the actuating mechanism can have the required number of levers and the like.

In order to achieve a defined starting position of the flexible section and/or easy connectability to a mating coupling piece, a restoring mechanism can be provided, which brings the adjusting element to a normal position in the absence of actuation. For example, the restoring mechanism can be formed by a spring or an elastic element.

In one embodiment of the invention, provision can be made that the handle is provided with a marking, which indicates the orientation of the insertion part with respect to rotations about the direction of extension of the latter. Thus, a person using the device can easily control and manipulate the orientation of the distal end of the insertion part in the cavity without visually monitoring the flexible section.

To form a flexible control line, provision can be made that the actuating mechanism is connected to the adjusting element via at least one secondary Bowden cable. The connection can be produced indirectly via a coupling or directly. Preferably, these secondary Bowden cables are likewise configured for two-way or four-way control.

Here, provision can be made that the at least one secondary Bowden cable of the actuating mechanism engages on the adjusting element or on a mating coupling piece at at least one secondary engagement point, of which the radial distance from a rotation point of the joint is different than the radial distance of a primary engagement point from the rotation point of the joint, at which primary engagement point the at least one Bowden cable arranged in the insertion part engages on the adjusting element. It is advantageous that, by means of the different radial distances, transmission ratios can be formed between the movement paths of the primary and secondary Bowden cables.

It is particularly expedient if the mating coupling piece is mounted in a second joint, which has a joint socket and a corresponding joint ball. It is advantageous that the mating coupling piece can easily follow the adjustment movements of the adjusting element when it is coupled into the adjusting element.

Here, provision can be made that the secondary Bowden cables are rigidly connected to the mating coupling piece. Thus, by coupling the mating coupling piece into the adjusting element, the secondary Bowden cables can easily be connected to the adjusting element.

Provision can be made that the joint socket and/or the joint ball of the second joint have/has a secondary contact surface, which secondary contact surface describes a portion of a cylindrical, spherical or ellipsoid surface. Here, provision can be made that a radius of curvature of this secondary contact surface is equal to the corresponding radius of curvature of the contact surface of the first joint, or, in order to achieve a transmission ratio of the adjustment paths, provision can be made that a radius of curvature of this surface is different than a radius of curvature of the contact surface of the first joint.

In order to ensure that connecting lines arranged in the guide channel and in the passage are affected as little as possible by adjustment movements of the adjusting element, provision can be made that the passage is routed through a rotation point of the first joint.

If appropriate, provision can be made that the mating coupling piece likewise has a passage which, in the coupled position, continues the passage of the adjusting element in the proximal direction and, if appropriate, likewise opens into a guide channel.

The invention is now described on the basis of illustrative embodiments, although it is not limited to these illustrative embodiments. Other illustrative embodiments arise from combining individual or multiple features of the claims with one another and/or with individual or multiple features of the illustrative embodiments.

DETAILED DESCRIPTION OF THE PREFERRED EMBODIMENTS

Figure 1:
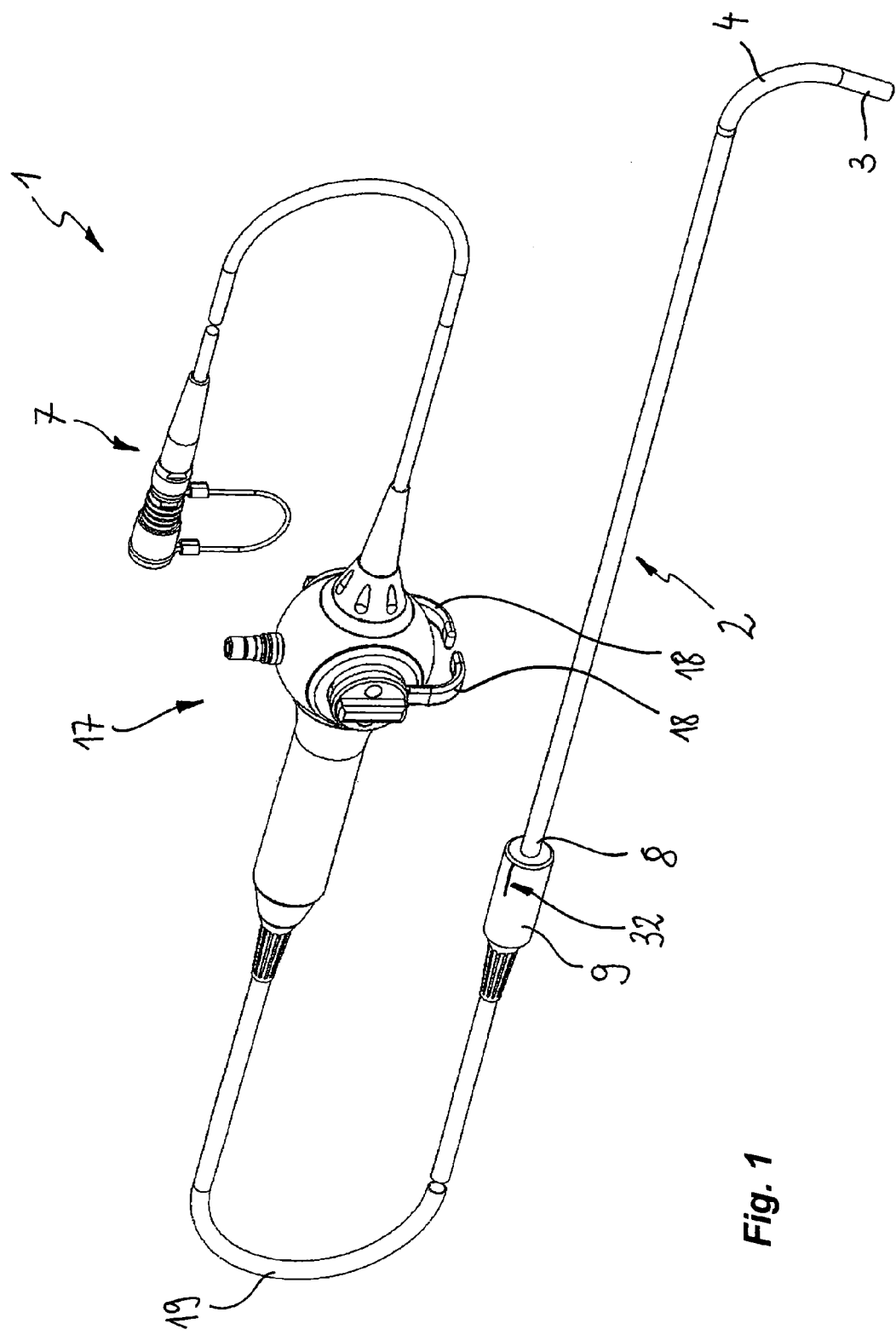
FIG. 1 shows a three-dimensional perspective view of a device according to the invention for monitoring and/or manipulating objects that are arranged in a cavity that can be accessed through a narrow opening.

In FIG. 1, reference number 1 designates a device for monitoring and/or manipulating objects that are arranged in a cavity that can be accessed through a narrow opening.

The device 1 has an insertion part 2, which is of tubular configuration, such that it can be inserted through the narrow opening into the cavity.

In the area of the distal end 3 of the insertion part 2, a flexible section 4 is formed on the insertion part 2, by means of which flexible section 4 the distal end 3 is connected movably to the rest of the insertion part 2.

Figures 2, 3:
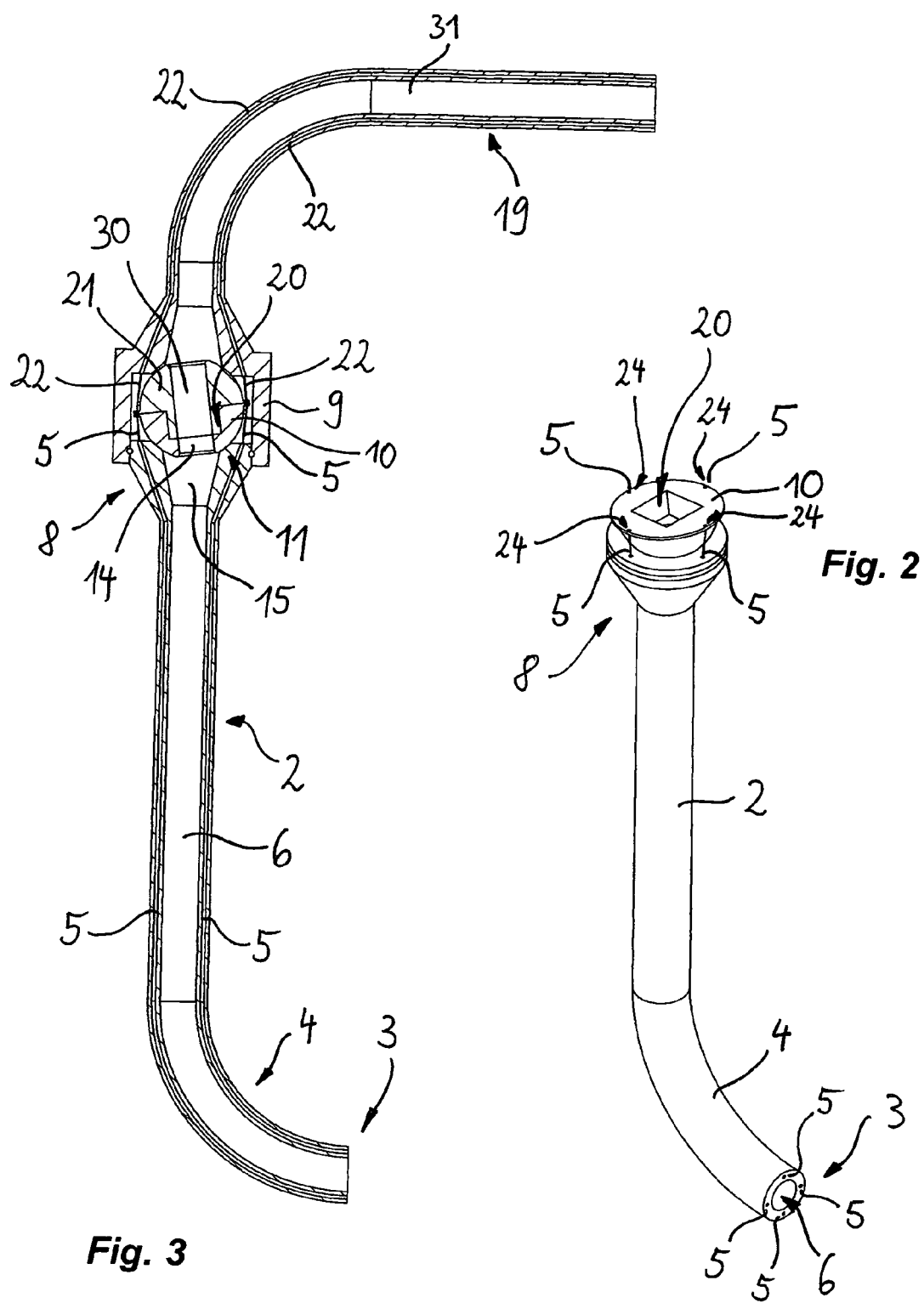
FIG. 2 shows a three-dimensional perspective view of an insertion part designed according to the invention.
FIG. 3 shows the insertion part according to FIG. 2 in a cross-sectional view.

The shape, in particular curve, of the flexible section 4, and therefore the position of the distal end 3, can be controlled via Bowden cables 5, which can be seen in FIG. 3 and which, in a manner known per se, are secured on the distal end 3 and guided through the insertion part 2.

The pair of Bowden cables 5 visible in FIG. 3 permit two-way control of the flexible section 4, and the cross arrangement of four Bowden cables 5 visible in FIG. 2 permits four-way control.

A guide channel 6, visible in FIG. 3, extends through the inside of the insertion part 2 and connects the distal end 3 to an attachment piece 7 of the device 1, such that the interior of the cavity is accessible from the direction of the attachment piece 7 by way of the inserted insertion part 2 and the guide channel 6 thereof. Here, the flexible section 4 can be bent such that the distal end 3 points in a desired direction.

Optical, mechanical and/or electrical connectors (not shown in detail) can thus extend through the guide channel 6 and be inserted into the cavity that is to be examined.

At the proximal end 8 of the insertion part 2, a handle 9 is formed, with which the insertion part 2 can be maneuvered.

Figure 6:
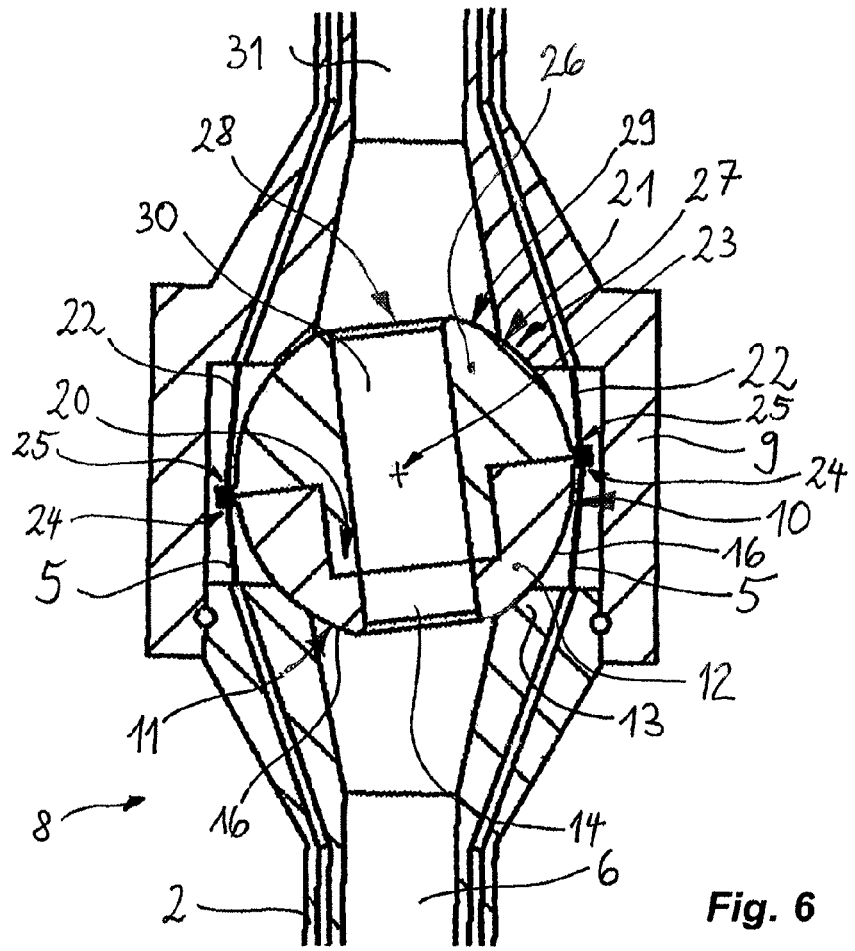
FIG. 6 shows a detail of the insertion part from FIG. 3.

An adjusting element 10 is arranged in the interior of the handle 9 at the proximal end 8 of the insertion part 2, as can be seen from FIG. 3 and from the detail in FIG. 6.

The adjusting element 10 and the distal end 8 of the insertion part 2 form a joint 11, wherein the adjusting element 10 is in the form of a joint ball 12, and a corresponding joint socket 13 is formed on the distal end 8. The joint ball 12 engages in the joint socket 13 and is mounted therein.

A passage 14 is formed as a bore in the adjusting element 10, such that the guide channel 6 is accessible from the attachment piece 7 by way of the adjusting element 10, since the passage 14 opens into the proximal end 15 of the guide channel 6 in the position of use.

In order to permit a sliding support of the adjusting element 10 in the joint socket 13, the joint ball 12 is designed with a spherical contact surface 16, by which the joint ball 12 acquires a spherical outer shape.

Since the Bowden cables 5 engage proximally on the adjusting element 10, the bending of the flexible section 4 can be varied by the adjustment of the adjusting element 10 in the joint socket 13.

For manual actuation of the adjusting element 10, the device 1 is provided with an actuating mechanism 17, which has actuating levers 18 connected to the handle 9 and to the adjusting element 10 via a flexible control line 19.

Here, the insertion part 2 can be connected to the flexible control line 19 by means of the proximal end 8 being fitted into the handle 9 and locked therein.

For transferring the control movement from the actuating mechanism 17 to the adjusting element 10 and thus onward to the flexible section 4, the adjusting element 10 is provided with a coupling point 20 into which, during use, a mating coupling piece 21 engages with a releasable form-fit.

Thus, a displacement of the mating coupling piece 21 is transferred to the adjusting element 10 and onward to the flexible section 4.

As is shown in more detail in FIG. 6, secondary Bowden cables 22 engage on the mating coupling piece 21 and can be controlled in four-way control via the actuating levers 18.

By means of the form-fit connection between adjusting element 10 and mating coupling piece 21, these secondary Bowden cables 22 are connected to the adjusting element 10 and thus transfer the manual actuation by the actuating mechanism 17. When the connection between adjusting element 10 and mating coupling piece 21 is released, the secondary Bowden cables 22 remain connected to the mating coupling piece 21, while the Bowden cables 5 remain connected to the adjusting element 10.

By virtue of the ball-shaped or spherical design of the contact surface 16, the joint 11 has a rotation point 23, about which the adjusting element 10 rotates when actuated.

The primary Bowden cables 5 of the insertion part 2 engage on the adjusting element 10 at primary engagement points 24, of which the radial distance from the rotation point 23 is equal to the radial distance of the secondary engagement points 25 of the secondary Bowden cables 22 on the mating coupling piece 21.

In the illustrative embodiment, the engagement points 24, 25 are even formed at corresponding opposite locations of the adjusting element 10 and of the mating coupling piece 21, respectively.

The equal radial distances have the effect that the adjustment movements of the secondary Bowden cables 22 are converted without change into corresponding adjustment movements of the (primary) Bowden cables 5.

The mating coupling piece 21 is in the form of a second joint ball 26 which, with a corresponding joint socket 27 of the handle 9, forms a second joint 28. Similarly to the situation in the joint 11, a spherical contact surface 29 is here formed on the joint ball 26 and slides in the joint socket 27.

The contact surfaces 29 and 16 together form a spherical surface, such that the rotation point of the second joint 28 is coincident with the rotation point 23 of the first joint 11. In this way, the contact surfaces 16, 29 also have matching radii of curvature.

The mating coupling piece 21 is also formed with a passage 30, which continues the passage 14 of the adjusting element 10.

The common passage 14, 30 is routed through the rotation point 23 of the joint 11 and connects the guide channel 6 to a secondary guide channel 31 in the flexible control line 19.

The secondary guide channel 31 is routed onward to the attachment piece 7 and there opens to the outside.

The insertion part 2 removable from the handle 5 is made of a sterilizable material.

Figures 4, 5:
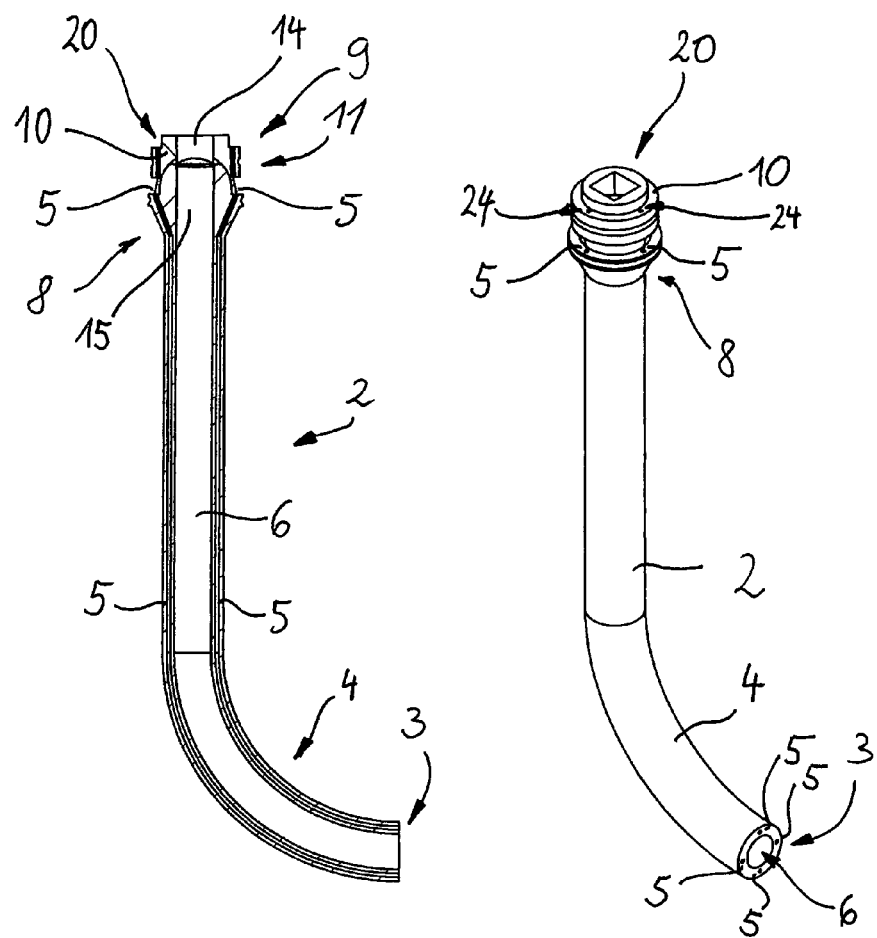
FIG. 4 shows a three-dimensional perspective view of another insertion part according to the invention.
FIG. 5 shows the insertion part according to FIG. 4 in a cross-sectional view.
Figure 7:
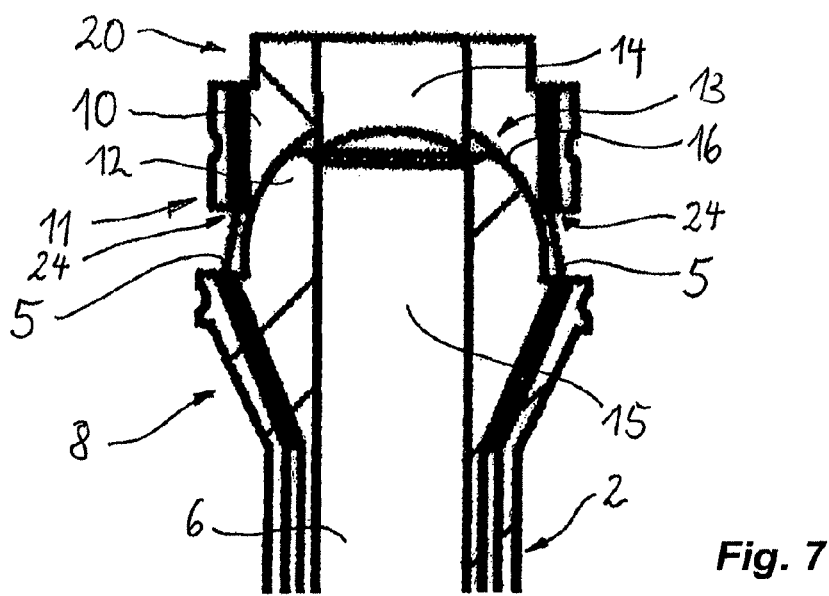
FIG. 7 shows a detail of the insertion part from FIG. 5.

FIGS. 4, 5 and 7 show another insertion part 2 which is designed according to the invention and which instead of the insertion part 2 from FIGS. 2, 3 and 6 can be connected to the handle 9.

In this insertion part 2, parts that have an equivalent function and/or design are designated by the same reference signs and are not separately described again.

The insertion part 2 according to FIGS. 4, 5 and 7 differs from the insertion part 2 according to FIGS. 2, 3 and 6 in that the joint ball 12 of the joint 11 is formed on the proximal end 8 of the insertion part 2, while the adjusting element 10 forms a joint socket 13.

In this way, the adjusting element 10 partially engages around the proximal end 8, as a result of which the adjusting element 10 is more accessible from the outside.

The insertion part 2 according to FIGS. 4, 5 and 7 can thus also be used without handle 9 and actuating mechanism 17, for example by means of a handpiece or the like being connected to the coupling point 20 of the adjusting element 10.

On the handle 9 of the device 1 in FIG. 1, there is also a marking 32, with which the orientation of the possibly bent distal end 3 in the cavity to be examined is indicated outside the opening.

In the device 1 for monitoring and/or manipulating objects that are arranged in a cavity that can be accessed through a narrow opening, a tubular or hose-shaped insertion part 2 is provided on which a flexible section 4 is formed which can be controlled via a Bowden cable 5, wherein the Bowden cable 5 engages on an adjusting element 10, which adjusting element 10 is mounted rotatably in a joint 11, which has a joint socket 13 and the adjusting element 10 in the form of a joint ball 12 that engages in this joint socket 13.

The invention claimed is:

1. A device (1) for at least one of monitoring or manipulating objects that are arranged in a cavity that can be accessed through a narrow opening, comprising a tubular or hose-shaped insertion part (2), a flexible section (4) formed on the insertion part (2), and at least one Bowden cable (5) for controlling the flexible section (4) arranged in the insertion part (2), the insertion part (2) contains a guide channel (6), adapted to receive at least one of optical, mechanical or electrical connectors for at least one of monitoring or manipulation, and an adjusting element (10) connected to the Bowden cable (5) to control the flexible section (4), wherein the adjusting element (10) is arranged on a proximal end (8) of the insertion part (2), a joint (11) including a joint socket (13) and the adjusting element in the form of a first joint ball (12) is mounted in the joint socket, and wherein the adjusting element (10) has a passage (14) that is adapted to receive the at least one of optical, mechanical or electrical connectors, and said passage (14) opens into a proximal end (15) of the guide channel (6) when the adjusting element (10) is in a position of use, a coupling point (20) for form-fit and releasable connection to a mating coupling piece (21) formed on the adjusting element (10), wherein a displacement of the mating coupling piece (21) is transferrable to the adjusting element (10) and onward to the flexible section (4), and the wherein mating coupling piece (21) is part of a second joint (28), which includes a second joint socket and the mating coupling piece (21) in the form of a second joint ball (26), and the first and second joint balls each have a contact surface (16, 29) that describes a portion of a spherical surface, the contact surfaces (16, 29), in the connected position, complement each other to form a ball surface.

2. The device (1) as claimed in claim 1, wherein the passage (14) is routed through a rotation point (23) of the joint (11).

3. The device (1) as claimed in claim 1, wherein an actuating mechanism (17) for manual actuation of the adjusting element (10) is provided, and the actuating mechanism (17) is connected to the adjusting element (10) via a flexible control line (19).

4. The device (1) as claimed in claim 1, wherein the adjusting element (10) is arranged in a handle (9) attached to the proximal end (8) of the insertion part (2).

5. The device (1) as claimed in claim 1, wherein at least one of the second joint socket (27) or the second joint ball (26) of the second joint (28) has a secondary contact surface (29), said secondary contact surface (29) describes a portion of a spherical surface.

6. The device (1) as claimed in claim 1, wherein a handle (9) for the insertion part (2) is arranged on a proximal end (8) of the insertion part (2), an actuating mechanism (17) for manual actuation of the adjusting element (10) is provided, and the actuating mechanism (17) is connected to the handle (9) via a flexible control line (19).

7. The device (1) as claimed in claim 6, wherein the handle (9) is provided with a marking (32), which indicates an orientation of the insertion part (2) with respect to rotations about a direction of extension of the latter.

8. A device (1) for at least one of monitoring or manipulating objects that are arranged in a cavity that can be accessed through a narrow opening, comprising a tubular or hose-shaped insertion part (2), a flexible section (4) formed on the insertion part (2), and at least one Bowden cable (5) for controlling the flexible section (4) arranged in the insertion part (2), the insertion part (2) contains a guide channel (6), adapted to receive at least one of optical, mechanical or electrical connectors for at least one of monitoring or manipulation, and an adjusting element (10) connected to the Bowden cable (5) to control the flexible section (4), wherein the adjusting element (10) is arranged on a proximal end (8) of the insertion part (2), a joint (11) including a joint socket (13) and the adjusting element in the form of a first joint ball, and the adjusting element (10) has a passage (14), said passage (14) adapted to receive the at least one of optical, mechanical or electrical connectors, and wherein said passage (14) opens into a proximal end (15) of the guide channel (6) when the adjusting element (10) is in a position of use, a coupling point (20) for form-fit and releasable connection to a mating coupling piece (21) formed on the adjusting element (10), wherein a displacement of the mating coupling piece (21) is transferrable to the adjusting element (10) and onward to the flexible section (4), and an actuating mechanism (17) connected to the adjusting element (10) via at least one secondary Bowden cable (22), wherein the at least one secondary Bowden cable (22) is connected to the adjusting element (10) by the form-fit connection between the adjusting element (10) and the mating coupling piece (21) and transmits a manual actuation by the actuating mechanism (17), and when the connection between the adjusting element (10) and the mating coupling piece (21) is released, the at least one secondary Bowden cable (22) remains connected to the mating coupling piece (21), while the primary Bowden cable (5) remains connected to the adjusting element (10).

9. The device (1) as claimed in claim 8, wherein the at least one Bowden cable (5) and at least one of the adjusting element (10) or the actuating mechanism (17) are designed for two-way or four-way control of the flexible section (4).

10. The device (1) as claimed in claim 8, wherein the actuating mechanism (17) is connected to the adjusting element (10) via the at least one secondary Bowden cable (22), or the at least one secondary Bowden cable (22) of the actuating mechanism (17) engages on the adjusting element (10) or on the mating coupling piece (21) at at least one secondary engagement point (25).

\* \* \* \* \*